US010273199B2

(12) United States Patent
Bernardin et al.

(10) Patent No.: US 10,273,199 B2
(45) Date of Patent: Apr. 30, 2019

(54) HYDROLYSIS VESSEL USED IN A PROCESS FOR AMIDIFICATION OF ACETONE CYANOHYDRIN (71) Applicant: Arkema France, Colombes (FR)

(72) Inventors: Yves Bernardin, Thionville (FR); Romain Billon, Carrieres sur Seine (FR); Xavier Marcarian, Billere (FR); Florent Vallet, Ecully (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 15/029,306

(22) PCT Filed: Oct. 17, 2014

(86) PCT No.: PCT/EP2014/072369
§ 371 (c)(1),
(2) Date: Apr. 14, 2016

(87) PCT Pub. No.: WO2015/055844
PCT Pub. Date: Apr. 23, 2015

(65) Prior Publication Data
US 2016/0251299 A1 Sep. 1, 2016

(30) Foreign Application Priority Data
Oct. 18, 2013 (FR) ...................................... 13 60194

(51) Int. Cl.
B01J 14/00 (2006.01)
B01J 19/18 (2006.01)
(Continued)

(52) U.S. Cl.
CPC ............... $C07C\ 67/20$ (2013.01); $B01J\ 4/002$ (2013.01); $B01J\ 14/00$ (2013.01); $B01J\ 19/002$ (2013.01);
(Continued)

(58) Field of Classification Search
None
See application file for complete search history.

(56) References Cited

U.S. PATENT DOCUMENTS 2,459,636 A * 1/1949 Fenney ................ B01J 19/0013
366/170.3
2,875,027 A * 2/1959 Dye .................... B01F 3/04531
165/109.1
(Continued)

FOREIGN PATENT DOCUMENTS

JP 59215588 A * 12/1984 ............. F28F 19/02
WO WO 03/016263 A1 2/2003

Primary Examiner — Jennifer A Leung
(74) Attorney, Agent, or Firm — Thomas F. Roland (57) ABSTRACT The invention relates to an hydrolysis vessel (200) used during amidification step of acetone cyanohydrin (ACH), in the industrial process for production of a methyl methacrylate (MMA) or methacrylic acid (MAA). The hydrolysis vessel (200) is used for hydrolyzing acetone cyanohydrine with sulfuric acid to produce a mixture comprising α-sulfatoisobutyramide (SIBAM). It comprises at least one cooling system (212; 244) on its internal annular periphery area and it is divided into at least two stages, preferably three, along its vertical wall, each stage (S1 to S3) comprising a ACH feeding inlet (201, 202, 203). Such vessel allows controlling both homogeneity and temperature of the mixture, and thus obtaining a high yield for the hydrolyzing reaction in very safe conditions.

18 Claims, 5 Drawing Sheets (51) Int. Cl.
*C07C 231/06* (2006.01)
*C07C 67/20* (2006.01)
*B01J 19/00* (2006.01)
*B01J 19/02* (2006.01)
*B01J 4/00* (2006.01)
*C07C 303/04* (2006.01)
*C07C 51/06* (2006.01)

(52) U.S. Cl.
CPC ......... *B01J 19/006* (2013.01); *B01J 19/0013* (2013.01); *B01J 19/0066* (2013.01); *B01J 19/02* (2013.01); *B01J 19/18* (2013.01); *B01J 19/1856* (2013.01); *B01J 19/1862* (2013.01); *C07C 51/06* (2013.01); *C07C 231/06* (2013.01); *C07C 303/04* (2013.01); *B01J 2219/0004* (2013.01); *B01J 2219/0027* (2013.01); *B01J 2219/00038* (2013.01); *B01J 2219/00058* (2013.01); *B01J 2219/00063* (2013.01); *B01J 2219/00065* (2013.01); *B01J 2219/00081* (2013.01); *B01J 2219/00092* (2013.01); *B01J 2219/00094* (2013.01); *B01J 2219/00162* (2013.01); *B01J 2219/00166* (2013.01); *B01J 2219/00272* (2013.01); *B01J 2219/00777* (2013.01); *B01J 2219/029* (2013.01); *B01J 2219/0245* (2013.01); *B01J 2219/0277* (2013.01); *B01J 2219/0286* (2013.01)

(56) References Cited

U.S. PATENT DOCUMENTS

| | | | |
|---|---|---|---|
| 2,939,770 A | | 6/1960 | Schwartzkopff et al. |
| 3,867,103 A | * | 2/1975 | Boney .................. B01J 14/00 422/230 |
| 3,951,386 A | * | 4/1976 | Small ................ B01F 15/00207 366/142 |
| 3,978,918 A | * | 9/1976 | Nagatomo ............ B01F 15/066 165/109.1 |
| 4,438,074 A | | 3/1984 | Wilt |
| 4,698,211 A | | 10/1987 | Storey et al. |
| 5,763,545 A | | 6/1998 | Takano et al. |
| 5,972,661 A | * | 10/1999 | Kubera ............... B01F 3/04609 261/123 |
| 6,024,481 A | | 2/2000 | Hillstrom et al. |
| 6,545,176 B1 | | 4/2003 | Tsay et al. |
| 7,511,101 B2 | * | 3/2009 | Nguyen ............... B01F 7/00291 165/109.1 |
| 2004/0022693 A1 | * | 2/2004 | Grady .................... C08F 2/001 422/105 |
| 2006/0111586 A1 | * | 5/2006 | Schladenhauffen .... C07C 51/06 564/123 |
| 2010/0305367 A1 | * | 12/2010 | Borremans ............. C07C 29/62 568/844 |
| 2010/0314239 A1 | * | 12/2010 | Gropp .................... C07C 51/06 203/35 |
| 2011/0178254 A1 | | 7/2011 | Matasuba et al. |

* cited by examiner

HYDROLYSIS VESSEL USED IN A PROCESS FOR AMIDIFICATION OF ACETONE CYANOHYDRIN

This application claims benefit, under U.S.C. § 119 or § 365 of PCT Application Number PCT/EP2014/072369, filed Oct. 17, 2014, and French Patent Application Number FR13.60194, filed Oct. 18, 2013, these documents being incorporated herein by reference.

FIELD OF THE INVENTION

The present invention relates to a continuous industrial process for the production of methyl methacrylate (MMA) or methacrylic acid (MAA). It relates more particularly to a step of such industrial process, which concerns the amidification step of acetone cyanohydrin. The invention relates more precisely to an hydrolysis vessel used during this amidification step for hydrolyzing acetone cyanohydrin with sulfuric acid to produce an amide, which is then thermally converted into a methacrylamide mixture, which is further either esterified to produce methyl methacrylate (MMA) or hydrolyzed in order to produce methacrylic acid (MAA).

STATE OF THE ART

A number of commercial processes are used to prepare monomer selected from methacrylic acid (also called "MAA" in the following description) and/or methyl methacrylate (also called "MMA" in the following description). One of these processes consists in preparing such monomer from acetone cyanohydrin (ACH). Such a process is for example described in US patent application US2010/0069662. In this process, acetone cyanohydrin ACH is hydrolysed by sulphuric acid to produce an hydrolysis mixture of α-hydroxyisobutyramide (also called "HIBAM" in the following description), its sulfate ester, α-sulfatoisobutyramide (also called "SIBAM" in the following description), 2-methacrylamide (also called "MAM" or "MACRYDE" in the following description) and methacrylic acid MAA. The hydrolysis mixture thus produced is then thermally converted, into a heated thermal conversion reactor, to a mixture comprising 2-methacrylamide MAM and a small amount of MAA.

The document EP0999200 discloses an apparatus and process for the high yield production of methyl methacrylate or methacrylic acid. The process comprises a cracker reactor including a plug flow thermal conversion apparatus and discloses as well hydrolysis reactors. However a cooling system for the required temperature range is not disclosed.

MAM can be used to produce MMA by reaction of esterification with methanol, or it can be used to produce MAA by reaction of hydrolysis with water.

Methyl methacrylate MMA is mostly used to produce polymer such as polymethylmethacrylate (also called "PMMA") which has multiple applications like for example automotive, transport, aerospace, photovoltaic, informatics, telecommunications, wind energy, or building construction. MMA can also be used to produce other methacrylates by mean of trans-esterification.

The MMA and MAA markets are extremely cost sensitive. A slight improvement in process yield can result in a significant market advantage.

Particularly, the first hydrolysis reaction during the step of amidification, has a very fast kinetics, which is typically of few seconds, and is very exothermic. The exothermic reaction may lead to the production of decomposition products such as acetone, CO and even HCN. If the mixing and the cooling system are not efficient, there is a large ACH and sulphuric acid decomposition with generation of gas, like CO or SO2. If the decomposition is not controlled, the temperature increases easily due to heat release by decomposition, and pressure increases due to gas generated in the reactor. A runaway reaction may occur if either the mixing system or the cooling system fails, which can lead to a breakage of the reactor. Therefore, the two key points for efficiency of the hydrolysis reaction is a good mixing and a good cooling system, which controls perfectly and keeps the temperature inside a certain interval, in order to avoid the decomposition or degradation of the products and improve the selectivity and yield of the reaction.

Generally, the hydrolysis reaction is produced in two reactors in series, each component of the reaction, namely ACH and sulphuric acid, are introduced through an inlet located at the top of the reactor, and an agitation shaft is driven in rotation, so that its impeller located at the bottom of the reactor homogenizes the mixture. The mixture is cooled down by a cooling device in form of a heat exchanger system placed downstream the reactors.

The applicant has discovered that such reactors do not give entire satisfaction. Indeed, the homogeneity and the cooling down of the mixture of components are not sufficiently well controlled, so that it appears a lot of decomposition products. This is due to the fact that the reaction is very fast, so that the mixture has not enough time to homogenize before completion of the reaction. There are creations of hot points in the mixture, which lead to apparition of decomposition products. Thus the yield of the reaction is low and it is usually lower than 90%.

Therefore, there is a need for improving the conditions for the hydrolysis reaction of the amidification step in order to increase the yield of the reaction.

Therefore, there is a need for improving the conditions for the hydrolysis reaction of the amidification step in order to control and regulate the temperature inside the reactor so that it is homogenous without hotspots in order to avoid decomposition and degradation into large quantities not wanted products.

Technical Problem

Present invention aims to avoid at least one of the inconvenient of the state of the art. More particularly, the invention aims to propose an improved hydrolysis vessel designed for better controlling both the homogenization and the cooling of the mixture of components, before the completion of the reaction, so as to improve the yield of the hydrolysis reaction.

BRIEF DESCRIPTION

For this purpose, the invention relates to a vessel for hydrolyzing acetone cyanohydrin (ACH) by sulfuric acid ($H_2SO_4$) to produce an hydrolysis mixture comprising α-sulfatoisobutyramide (SIBAM), said vessel comprising an agitation system for homogenizing the mixture, said vessel being characterized in that it comprises at least one cooling system on its internal annular periphery area and it is divided into at least two stages, along its vertical wall, each stage comprising a ACH feeding inlet.

The vessel according to the invention with the cooling system on its internal annular periphery area, avoids that the complete thermal exchange of the hydrolyses mixture has to be made via the periphery area, by an outside cooling jacket, which is slow in regulation.

Thus, the fact to provide a cooling system inside the vessel and to split the feeding of ACH through two or more feeding inlets allows avoiding creation of hot points. Indeed, ACH has the time to homogenize with sulfuric acid before completion of the hydrolysis reaction, and the cooling system being inside the vessel it allows controlling the temperature inside the vessel and avoiding the creation of hot points.

According to another aspect, the invention relates to a unit for amidification of acetone cyanohydrin (ACH) into a mixture comprising 2-methacrylamide (MACRYDE), said unit comprising a first installation for hydrolyzing acetone cyanohydrin (ACH) by sulfuric acid to produce an hydrolysis mixture comprising α-sulfatoisobutyramide (SIBAM), heating means for heating said hydrolysis mixture at a temperature comprised between 110° C. and 165° C., and a thermal conversion vessel for thermally converting said hydrolysis mixture into said mixture comprising 2-methacrylamide (MACRYDE), said unit being characterized in that said first installation comprises at least one vessel as described above.

Preferably, first hydrolysis installation comprises at least two vessels in parallel and functioning simultaneously.

According to another aspect, the invention relates to a process for amidification of acetone cyanohydrine (ACH) comprising a first step of hydrolyzing acetone cyanohydrine by sulphuric acid to produce an hydrolysis mixture comprising α-sulfatoisobutyramide (SIBAM), and a second step of thermally converting said hydrolysis mixture into a mixture comprising 2-methacrylamide (MACRYDE), said process being characterized in that said first hydrolyzing step comprises following steps:
  feeding vessel described above, with $H_2SO_4$ by a bottom inlet of said vessel and with ACH by at least two different injection inlets distributed along the vertical wall of the vessel,
  simultaneously to injection of ACH, homogenize the mixture with the agitation system of said vessel,
  managing the temperature inside the vessel, by means of at least one cooling system, said temperature having to be comprised between 80° C. and 110° C., preferably between 85° C. and 100° C.

Finally, invention relates to a process for preparing a monomer selected from methacrylic acid (MAA) and/or methyl methacrylate (MMA) comprising the steps of:
  preparing hydrogen cyanide (HCN) by the Andrussow process,
  preparing acetone cyanohydrin (ACH) from hydrogen cyanide and acetone,
  hydrolyzing acetone cyanohydrin (ACH) to produce an hydrolysis mixture comprising α-hydroxyisobutyramide, α-sulfatoisobutyramide, 2-methacrylamide and methacrylic acid,
  thermally converting said hydrolysis mixture in a thermal conversion apparatus with a necessary retention time to produce a mixture comprising 2-methacrylamide,
  reacting the obtained mixture comprising 2-methacrylamide in at least one reactor with a material selected from methanol or water to produce a monomer respectively selected from methyl methacrylate (MMA) or methacrylic acid (MAA), said process being characterized in that the step (S4) of hydrolyzing acetone cyanohydrin (ACH) is made according to process for amidification of acetone cyanohydrin described above by using the vessel described above.

INTRODUCTION OF THE FIGURES

Other features and advantages of the invention will become apparent upon reading the following description given by way of illustrative and non-limiting examples, with reference to the accompanying Figures in which.

SPECIFICATION

The hydrolysis vessel described in the specification has a substantially cylindrical shape, the height of the cylinder defining the vertical axis of the vessel, perpendicular to the ground on which it is placed, and the diameter defining the horizontal axis, parallel to the ground.

The terms "top", "upper" or "above" and "down", "bottom", or "below" are used to define a portion of the vessel with respect to the vertical axis of said vessel.

Figure 1:
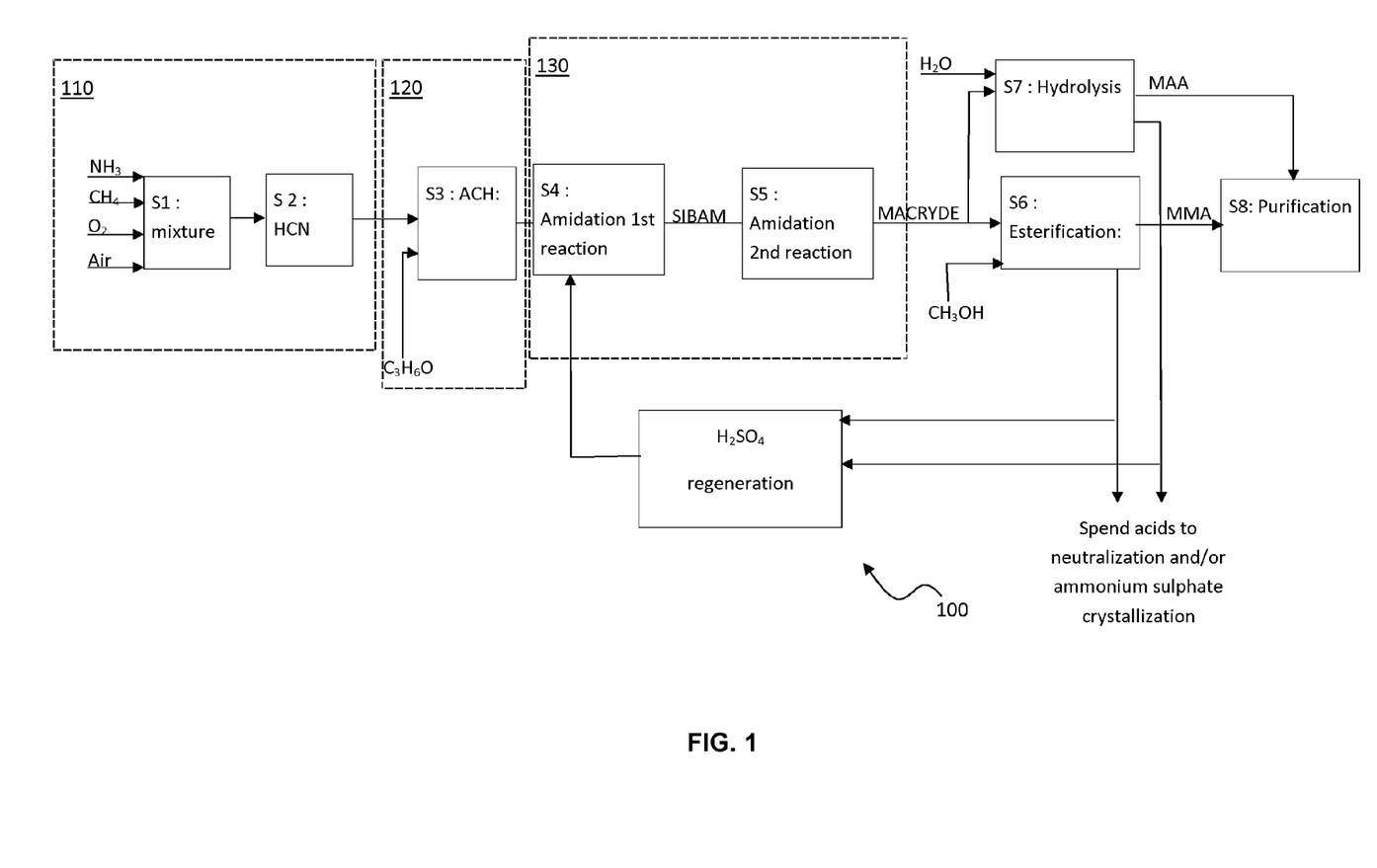
FIG. 1 represents a simplified schematic bloc diagram of a plant for preparing methacrylic acid and/or methyl methacrylate.

The terms "upstream" and "downstream" are defined relative to the direction of a fluid flowing through the devices of a plant for the production of a final product such as methyl methacrylate (MMA) or methacrylic acid (MAA). Concerning the Synthesis of Monomer Selected From Methacrylic Acid and/or its Esters FIG. 1 shows a simplified schematic bloc diagram of a plant for the production of methacrylic acid and/or its esters from acetone and hydrogen cyanide HCN prepared by the Andrussow process. The Andrussow process is for example described in the document U.S. Pat. No. 1,934,838.

Such monomers can be further used to produce for example polymethylmethacrylate (PMMA) that is a polymer widely used in a lot of applications like for example automotive, transport, aerospace, photovoltaic, informatics, telecommunications, wind energy, or building construction . . .
Preparation of Hydrogen Cyanide HCN First of all (steps S1 and S2) HCN is produced in a first unit 110, from a mixture of methane-containing gas, ammonia and air eventually enriched with oxygen. A mixture of reactant gases is prepared (step S1), and introduced (step S2) into an Andrussow type reactor comprising catalyst gauzes based on platinum/rhodium gauzes. Mixture of gases passes over the catalyst gauzes and reacts at a temperature comprised between 750° C. and 1250° C. and preferably between 1000 and 1200° C., to form HCN. The oxygen-enriched air enables to increase the productivity and to reduce the methane consumption. The HCN produced is quickly cooled and treated so as to avoid polymerization of HCN. For that, ammonia which has not reacted is absorbed by reaction with sulfuric acid, and the HCN is absorbed and stabilized in an absorption column, and then distilled in a distillation column to reach a purity of 99.5% wt.

Preparation of Acetone Cyanohydrin ACH

The thus synthesized HCN is then mixed with acetone ($C_3H_6O$), in a unit 120 designed for the production of acetone cyanohydrin ACH (step S3). The crude acetone cyanohydrin obtained is then purified by distillation.

Amidification of Acetone Cyanohydrin

A third unit 130 of the plant is provided for amidification of acetone cyanohydrin. Such amidification of ACH requires two steps S4 and S5 for producing 2-methacrylamide (also called "MACRYDE" in the following description).

First, in step S4, sulphuric acid ($H_2SO_4$) is added in excess in comparison with acetone cyanohydrin ACH. For example the molar ratio of $H_2SO_4$/ACH is comprised between 1.2 and 2, preferably between 1.25 and 1.8, and more preferably between 1.3 and 1.6.

This first reaction occurring is an hydrolysis reaction of ACH by sulphuric acid, which gives an intermediate salt, called the SIBAM (for α-sulfatoisobutyramide). This reaction is the following:

$$(CH_3)_2COHCN + H_2SO_4 \rightarrow (CH_3)_2COSO_3HCONH_2$$
Acetone cyanohydrin(ACH)α-sulfatoisobutyramide (SIBAM) (1)

This reaction is fast and exothermic. The temperature is comprised between 80 and 110° C. and the pressure is close to the atmospheric pressure.

The second reaction (step S5) is a slow and endothermic reaction. It occurs at atmospheric pressure and a temperature range between 110 and 165° C., preferably between 125° C. and 150° C. and more preferably between 130 and 145° C. This reaction is a cooking reaction which lasts between 3 and 16 minutes. This reaction is the following:

$$(CH_3)_2COSO_3HCONH_2 \rightarrow CH_2C(CH_3)CONH_2 + H_2SO_4$$
α-sulfatoisobutyramide(SIBAM)2-methacrylamide (MACRYDE) (2)

During the synthesis reactions there are many other by-products. The main side reaction is described below.

The first hydrolysis reaction of ACH by a small quantity of water can create a significant quantity of HIBAM (α-hydroxyisobutyramide). Such a reaction is very fast. It is the following:

$$(CH_3)_2COHCN + H_2O \rightarrow (CH_3)_2COHCONH_2$$ Acetone cyanohydrin(ACH)α-hydroxyisobutyramide (HIBAM) (3)

In the second step S5, HIBAM can also create MACRYDE, but this reaction is very slow. So there is a large quantity of unconverted HIBAM at the end of amidification step S5. The reaction is the following:

$$(CH_3)_2COHCONH_2 \rightarrow CH_2C(CH_3)CONH_2 + H_2O$$
α-hydroxyisobutyramide(HIBAM) methacrylamide(MACRYDE) (4)

The hydrolysis of HIBAM may create HIBA (α-hydroxyisobutyricacid)

$$(CH_3)_2COHCONH_2, H_2SO_4 + H_2O \rightarrow (CH_3)_2COHCOOH + NH_4HSO_4$$ α-hydroxyisobutyramide(HIBAM)α-hydroxyisobutyricacid (HIBA)+ammoniumbisulfate (5)

At the same time, a significant amount of methacrylic acid MAA is produced by the hydrolysis of SIBAM by water. This reaction is the following:

$$(CH_3)_2COSO_3HCONH_2H_2O \rightarrow CH_2C(CH_3)COOH + NH_4HSO_4$$ α-sulfatoisobutyramide(SIBAM) methacrylic acid(MAA)+ammoniumbisulfate (6)

The mixture of MACRYDE and MAA, also called mixture comprising 2-methacrylamide, obtained after amidification is then either hydrolyzed (step S7), by adding water to the MACRYDE mixture, or esterified (step S6), by adding methanol to the MACRYDE mixture.

Esterification

The components obtained after amidification, namely the methacrylamide and the methacrylic acid, are esterified, so as to obtain methyl methacrylate MMA. The esterification reaction (step S6) is made by mixing said components with methanol ($CH_3OH$).

The main reactions are these two below:

$$CH_2C(CH_3)CONH_2, H_2SO_4 + CH_3OH \rightarrow CH_2C(CH_3)COOCH_3 + NH_4HSO_4$$ methacrylamide(MACRYDE)+methanol methyl methacrylate(MMA)+ammoniumbisulfate (7)

$$CH_2C(CH_3)COOH + CH_3OH \rightarrow CH_2C(CH_3)COOCH_3 + H_2O$$ methacrylic acid(MAA)+methanol methyl methacrylate (MMA) (8)

Hydrolysis

The components obtained after amidification can also be hydrolysed by mixing them with water (step S7). Such hydrolysis reaction allows to obtain methacrylic acid according to the following reaction:

$$CH_2C(CH_3)CONH_2, H_2SO_4 + H_2O \rightarrow CH_2C(CH_3)COOH + NH_4HSO_4$$ methacrylamide(MACRYDE) methacrylic acid (MAA)+ammoniumbisulfate (9)

Purification of Crude MMA or MAA Obtained

Either the crude methylmethacrylate MMA obtained after esterification (S6) or the crude methacrylic acid MAA obtained after hydrolyse (S7) is then purified (step S8) by classical process known in the art, in order to remove residual compounds.

Used $H_2SO_4$ from esterification or hydrolysis may be used to produce ammonium sulfate or may be regenerated to produce sulfuric acid/oleum which can be recycled into the process.

Concerning the Hydrolysis Step by Means of an Hydrolysis Vessel

Figure 2:
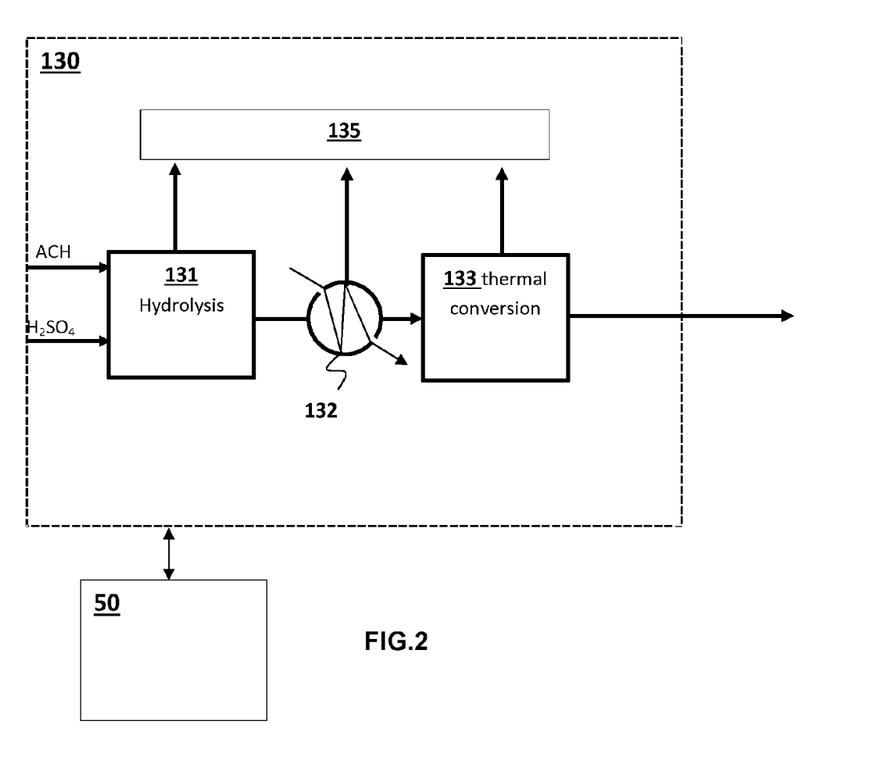
FIG. 2 represents a simplified schematic bloc diagram of a portion of plant of FIG. 1, corresponding to amidification section of the plant.

FIG. 2 shows a simplified schematic bloc diagram of a portion of plant of FIG. 1, corresponding to amidification unit 130 of the plant. This unit 130 comprises first installation 131 for hydrolyzing acetone cyanohydrin ACH by sulphuric acid $H_2SO_4$, to produce the hydrolysis mixture comprising α-sulfatoisobutyramide (SIBAM) (see step S4 of the process for production of MMA or MAA). The thus synthesized hydrolysis mixture is then thermally converted into a mixture comprising 2-methacrylamide (MACRYDE) and a small amount of methacrylic acid (MAA). For that, the amidification unit 130 comprises heating means 132 for heating the hydrolysis mixture comprising SIBAM at a temperature which has to be comprised between 110° C. and 165° C., preferably between 125° C. and 150° C. and more preferably between 130° C. and 145° C., in order to ensure an optimal conversion of the hydrolysis mixture. Such heating is provided by means of a heat exchanger 132, functioning with a heating stream. The heated hydrolysis mixture is introduced into a thermal conversion vessel 133 for a predetermined retention time. The thermal conversion vessel is a confined vessel inside which the mixture is maintained at the conversion temperature during the predetermined retention time to have an optimal yield of conversion. When the retention time is reached, the mixture comprising 2-methacrylamide flows through at least one outlet valve of the thermal conversion vessel.

Then the obtained mixture comprising 2-methacrylamide is quickly directed to next reaction step (step S6 or S7 in FIG. 1) of the process for preparing a monomer selected from methacrylic acid and/or methyl methacrylate, in order to avoid its polymerization. Optionally, it is possible to provide cooling means immediately downstream the thermal conversion vessel.

Each of the equipment of this amidification unit 130, namely the hydrolysis installation 131, the heating means 132, and the thermal conversion vessel 133 is equipped with at least one vent connected to a vent collection network 135, in order to discharge the gases that form due to the decomposition of the components of the mixtures in course of the amidification process.

A control unit referenced 50 on FIG. 2 allows controlling temperature inside the equipments of the amidification unit, feeding flowrates, and also cooling temperature of the cooling systems. This control unit is described in more details in regards with the hydrolysis vessel.

Figure 3:
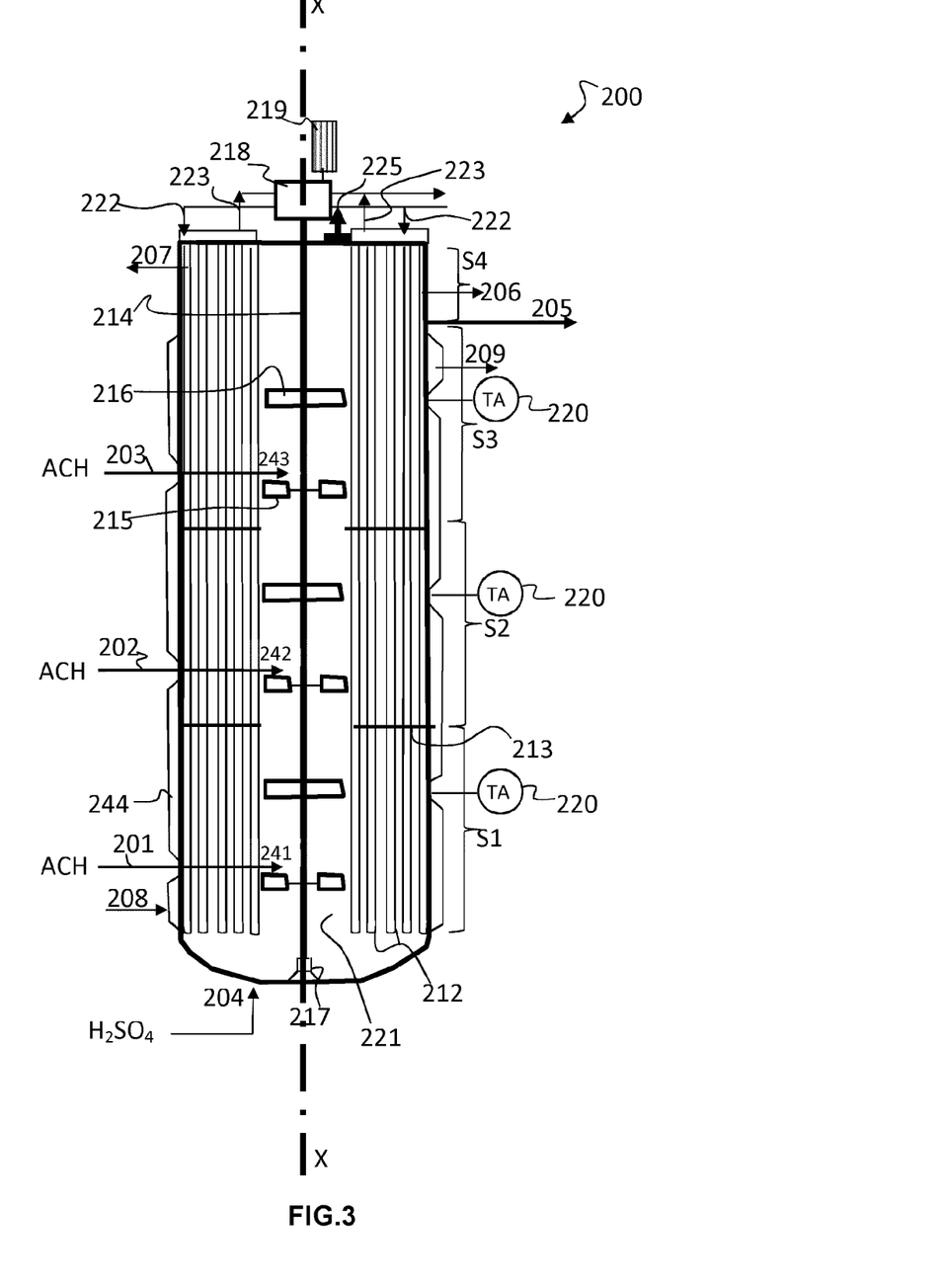
FIG. 3 represents a schematic sectional view of an hydrolysis vessel of the invention.
Figure 5:
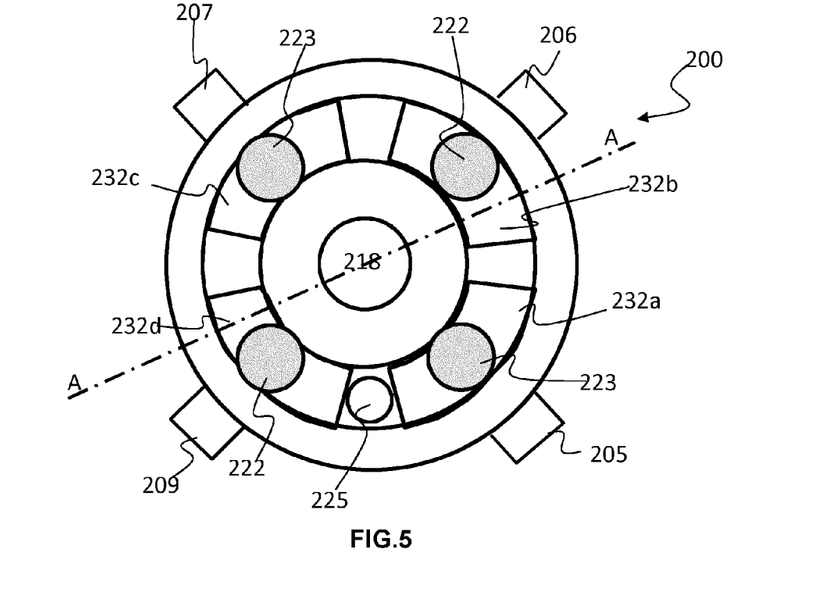
FIG. 5 represents a schematic top view of the hydrolysis vessel of FIG. 3.

FIG. 3 shows in more details a schematic cross sectional view A-A (FIG. 5) along a vertical axis X-X of an hydrolysis vessel 200 according to the invention.

This hydrolysis vessel 200 has a substantially cylindrical shape, whose height defines a vertical axis X-X perpendicular to the ground on which it is placed. Thus, the horizontal axis, parallel to the ground, is defined by the diameter of the cylinder.

The hydrolysis reaction of ACH with sulphuric acid, to produce SIBAM is highly exothermic and can entail hot points. These hot points may increase decomposition rate into gaseous components and so decrease yield of SIBAM/ACH. To avoid these hot points, the applicant has discovered that it is better to split ACH injection points in sulphuric acid. Therefore, the vessel comprises at least two or more ACH inlets. Preferably, it comprises three inlets 201, 202, 203 distributed along the vertical wall of the vessel.

Moreover, in order to have more ACH inlets, one or more parallel vessels can be added. More preferably, the hydrolysis reaction can be conducted into two vessels 200 in parallel, functioning simultaneously.

The hydrolysis vessel 200 is advantageously divided into at least two stages (S1, S2, . . . , $S_x$), and preferably three stages S1, S2, S3. Each stage comprises one ACH feeding inlet respectively 201, 202, 203. The plurality of ACH feeding inlets enables to homogenize quicker ACH in the sulfuric acid, which is injected through an inlet 204 provided at the bottom of the vessel 200. This homogenization of the mixture is important to avoid hot points.

Sulfuric acid is fed in the bottom of vessel and the overall flow inside the vessel 200 flows from the bottom to the top. The hydrolysis mixture containing SIBAM exits from the vessel 200 through an overflow outlet nozzle 205 located at the upper part of the vessel, namely at top of the upper stage S3. The hydrolysis mixture containing SIBAM then flows towards the heating means and the thermal conversion vessel for the second reaction of amidification. Above the upper stage S3 and the liquid overflow outlet nozzle 205, there is a space S4 designed for gas phase issued from decomposition of ACH during the hydrolysis reaction. A gas outlet nozzle 206 can be provided above liquid outlet nozzle 205, and be connected to a vent collecting network.

An emergency outlet nozzle 207 may be added to protect this reactor against runaway reaction and overpressure. The vessel comprises also a safety equipment, like a bursting disk 225 located on top of the vessel, in order to discharge overpressure in case of runaway reaction, and to avoid a breakage of the vessel. Such bursting disk 225 is schematized on FIGS. 3 and 5.

The internal annular periphery of the vessel comprises a first cooling system made of tubes bundle 212 as described here below. The cooling system made of tubes bundle comprises between 10 and 50 000 tubes, preferably between 16 and 40 000 tubes and more preferably between 20 and 30 000 tubes. A free central area 221 of the vessel is designed to receive an agitation system 214 and to let the mixture flowing upward towards the overflow outlet nozzle 205. This central area 221 measures between 40% and 80% of the vessel diameter. The vessel diameter is the distance between the internal annular peripheries of the vessel of each side at the line AA on FIG. 5. The reaction mixture circulates between free central area 221, the tubes bundle 212 inside the vessel 200 and internal annular periphery.

The agitation system comprises a shaft 214, which is fixed on a support 217 located at the bottom of the vessel 200. The shaft 214 is driven in rotation by means of a motor 219 located above the vessel 200. A reduction gearbox 218 is also placed between motor and shaft 214 of agitation system, in order to control the rotation speed of the shaft.

For each stage S1 to S3 of the vessel, the agitation system comprises advantageously two impellers 215, 216. A first impeller is a radial flow impeller 215, while the second impeller is an axial flow impeller 216. Radial flow impeller 215 ensures good homogenization between ACH and sulphuric acid, and ensures high turbulence of the viscous mixture. Axial flow impeller 216 ensures good volumetric flow inside each stage and between stages. More preferably, for each stage S1 to S3 of the vessel 200, axial flow impeller 216 is located above radial flow impeller 215. For example radial flow impeller can be, but not limited to, turbine type agitator whereas axial flow impeller can be, but not limited to, propeller type agitator. So, for a vessel comprising three stages S1 to S3 and three ACH inlets 201 to 203, there are at least 6 impellers on the same shaft 214. Thus, the agitation system ensures an efficient homogenization and an efficient heat exchange rate between reaction mixture and the first cooling system located at the internal annular periphery of the vessel.

For each stage, the ACH inlet 201, 202, 203 further comprises an injection nozzle, whose outlet 241, 242, 243 is close to the shaft 214, i.e. whose outlet is located in the central area 221 of the vessel, and more preferably close to the radial flow impeller 215 and more preferably just above radial flow impeller 215. Injection of ACH close to the shaft and preferably just above radial flow impeller 215 enables to homogenise very quickly ACH in sulphuric acid, simultaneously to its injection.

In order to control the heat generated by the exothermal reaction at least one cooling system is provided inside the vessel. A first cooling system comprises vertical tubes bundle 212, set up in the peripheral internal annular area of the vessel, said tubes extending on the whole height of the vessel and comprising U-bends at their bottom. This tubes bundle is traversed by a cooling water stream. Tubes are connected to the top plate of the vessel, which is schematized by its top view on FIG. 5. Cooling water inside tubes bundle is a two pass system. There are several tens or several hundred of tubes. At the top of the vessel, at least one feeding duct 222 is provided for feeding the tubes bundle 212 of the first cooling system with cooling water and at least one collecting duct 223 is provided to recover hot water exiting from tubes bundle 212. Preferably, it comprises two feeding ducts 222 and two collecting ducts 223 alternatively distributed on the vessel top surface as illustrated on FIG. 5.

Preferably, in order to better control the temperature of the reaction and to limit hot points inside the vessel, a second cooling system is provided across the external jacket 244 of the vessel. The jacket covers the whole external surface of stages S1 to S3, corresponding to the liquid area inside the vessel. This jacket 244 is traversed by cooling water stream, which flows from a bottom inlet 208 to the top of the upper liquid stage S3 of the vessel 200, where an outlet 209 recovers the hot water towards a condenser system.

The cooling system is part of a closed loop of water. Such closed loop, formed with pipes 303, 304, is schematized on FIG. 4, on which two parallel hydrolysis vessels 200a, 200b functioning simultaneously are represented. Softened water or demineralised water is preferably used in order to avoid fooling in water side due to scale deposit because of high temperature. The temperature of the cooling water has to be maintained above 60° C. and below 90° C. Indeed, at low temperature, reaction mixture, and more particularly the obtained SIBAM, may crystallize. Therefore cooling system is preferably not done with cooling water below 60° C. to avoid superficial crystals deposit on tubes of first cooling system or jacket of second cooling system.

Figure 4:
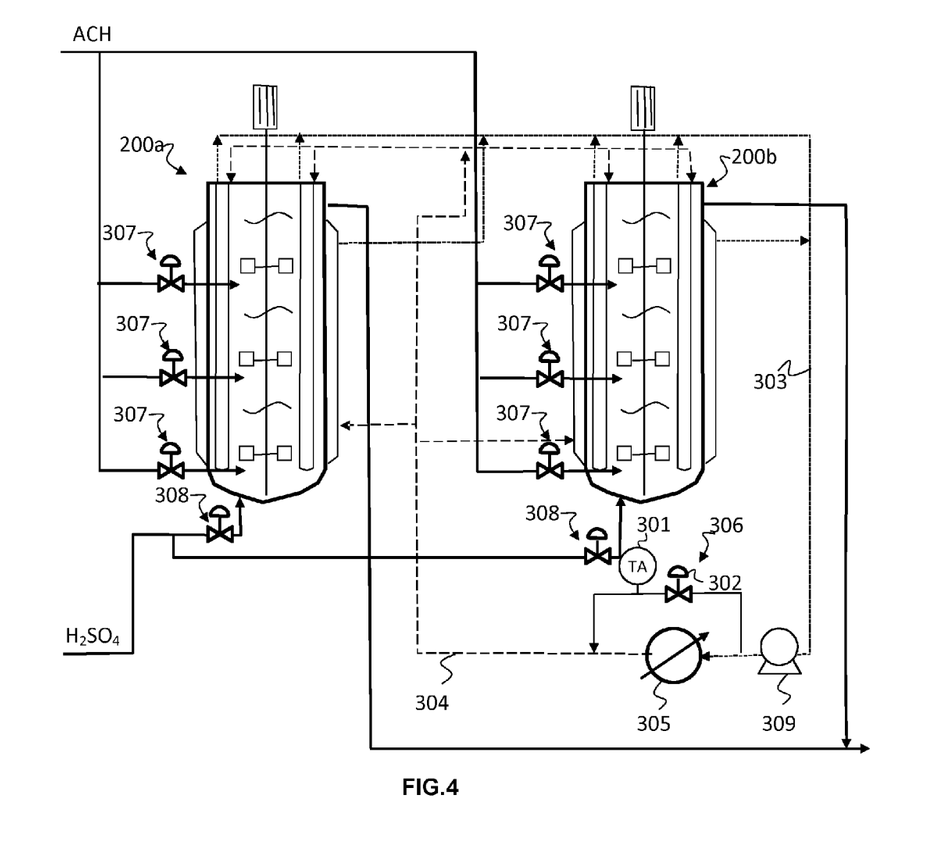
FIG. 4 represents a schematic view of an installation comprising two hydrolysis vessels in parallel and a closed loop of water for feeding at least one cooling system of each vessel.

At the bottom of the loop, there is at least one circulation pump 309 for injecting water into cooling system with a very high flowrate. Typically, the flowrate has to be sufficient high that the temperature difference between the water entering and leaving the cooling system is lower than 12° C. and preferably lower than 8° C., in order to maintain a good temperature control of the water and to avoid vaporization of the water in contact with hot points. A heat exchanger 305 is also placed downstream the vessels between hot demineralised water pipe 303, coming from collecting ducts 223 and the outlet 209 of second cooling system, and cooling water pipe 304 for feeding the cooling systems of each vessel. Thus the heat exchanger 305 removes the heat of the water exiting the cooling systems, before its re-injection into said cooling systems. Reference 303, represented in dotted lines on FIG. 4, illustrates the pipes of hot water exiting the cooling systems, while reference 304 represented in dashed lines illustrates the pipes of cooled water designed to feed the cooling systems. Moreover, a by-pass 306 of the heat exchanger with a control valve 302, and a temperature sensor 301 connected to an alarm, is required to avoid too low temperature of the water. The cooling down of the cooling water is regulated and depends on the heat generated by the exothermal reaction inside the vessel. After the heat exchanger 305, the demineralised water is distributed to first and second cooling systems 212, 244 of each vessel 200a, 200b. Cooling systems shall be equipped with temperature and pressure sensors, for temperature and pressure measurements upward and downward the cooling systems of the vessel.

Thanks to the cooling systems, the operating temperature inside the vessel is well controlled and maintained between 80 and 110° C. and more preferably between 85° C. and 100° C. A temperature sensor TA, referenced 220 on FIG. 3, is advantageously disposed at each stage S1 to S3 of the vessel for controlling the temperature at each stage. The temperature sensors are connected to an alarm in case of an increase of the temperature.

Pressure measurement is normally made, by means of a pressure sensor, in the vent outlet 206, in order to control the pressure inside the vessel and to avoid a runaway of the reaction. Operating pressure at the top of the reactor in the gas phase is preferably but not exclusively between 0 barg and 0.5 barg, i.e between 0 and 0.5 bar above the atmospheric pressure.

Between each stage of the vessel 200, there is a plate baffle referenced 213 on FIG. 3. This baffle allows separating each stage S1 to S3 from the other. This baffle is represented on the scheme of FIG. 6, where it is referenced 230. It comprises a free central area 231 through which the liquid mixture can flow upwards inside the vessel 200 and through which the agitation system 214 can be placed. This plate baffle comprises also holes 233, in its peripheral annular area, distributed in four areas 232a to 232d, for inserting the tubes of the first cooling system 212. Thus, each plate baffle allows avoiding too much vibration of the tubes. Two holes areas 232a, 232c, opposite to each other, are placed under the feeding ducts 222 of cooling water, while other alternate areas 232b, 232d are placed below collecting ducts 223 and are traversed by cooling water, which is recovered by collecting ducts 223 at the top of the vessel.

Hydrolysis reaction of acetone cyanohydrin is done with pure ACH. Purity is higher than 98 wt %, more preferably higher than 99 wt %, more preferably higher than 99.5 wt %. Indeed impurities like water or acetone may generate liquid by-products, like HIBAM for example, or large quantity of gaseous components.

Sulphuric acid concentration is higher than 98 wt %, more preferably higher than 99%, and more preferably between 99.5 wt % and 100.0 wt %. Indeed water may entail larger quantity of HIBAM at the end of amidification step and therefore it entails large quantity of methyl alpha-hydroxy isobutyrate in case of downstream esterification, or a large quantity of acid alpha-hydroxy isobutyric in case of downstream reaction with water. Thus, purity of $H_2SO_4$ is preferably higher than 99.5 wt %. Its purity has also to be less than 100.0 wt %, in order to avoid other decomposition reactions and polycondensation reactions that may occur with such strong oxidant acid.

When 1 mole of ACH reacts with 1 mole of sulphuric acid to form SIBAM, reaction mixture becomes highly viscous due to disappearance of free sulphuric acid. Therefore it is required to put an excess of sulphuric acid in comparison with ACH. Minimum $H_2SO_4$/ACH molar ratio is 1.2, preferably this ratio is more than 1.25, and more preferably more than 1.3. In the other hand, a large excess of sulphuric acid entails a large quantity of spent acid to treat in downstream esterification step or hydrolysis step. Therefore, maximum $H_2SO_4$/ACH molar ratio has to be not more than 2 and more preferably not more than 1.8, and more preferably not more than 1.6.

A control unit, schematized under reference 50 on FIG. 2, allows regulating the feeding flowrates of the components. For that, the control unit advantageously comprises a calculator. The feeding flowrates of ACH are regulated and measured, by means of flowmeters and valves 307 (as schematized on FIG. 4), and the calculator adjusts the feeding flowrate of sulphuric acid, depending on the measured flowrate of ACH, so as to be compliant with a set value of the molar ratio of $H_2SO_4$/ACH. A feeding valve connected to a flowmeter as schematized under reference 308, and controlled by the control unit, allow the regulation of the feeding of sulphuric acid.

The control unit allows also managing the regulation of temperature of each cooling system and the regulation of the temperature inside each stage S1 to S3 of the vessel 200. The temperature sensors 220 are connected to an alarm if an increase of temperature is measured. A measurement of the intensity of the motor 219 driving the agitation shaft 214 is also controlled, in order to detect an increase of the viscosity of the mixture. Such measurement is connected to an alarm. If the motor intensity is too high, it means that the mixture becomes too much viscous, and that there is not enough sulphuric acid.

Inhibitor soluble in sulphuric acid, like phenothiazine or other inhibitor of polymerization is preferably introduced to prevent methacrylamide polymerization. It is mixed with sulphuric acid before feeding the vessel with said sulphuric acid.

Vessel materials include preferably, but not limited to, austenitic alloy or austeno ferritic alloy, INCOLOY or tantalum alloys.

Figure 6:
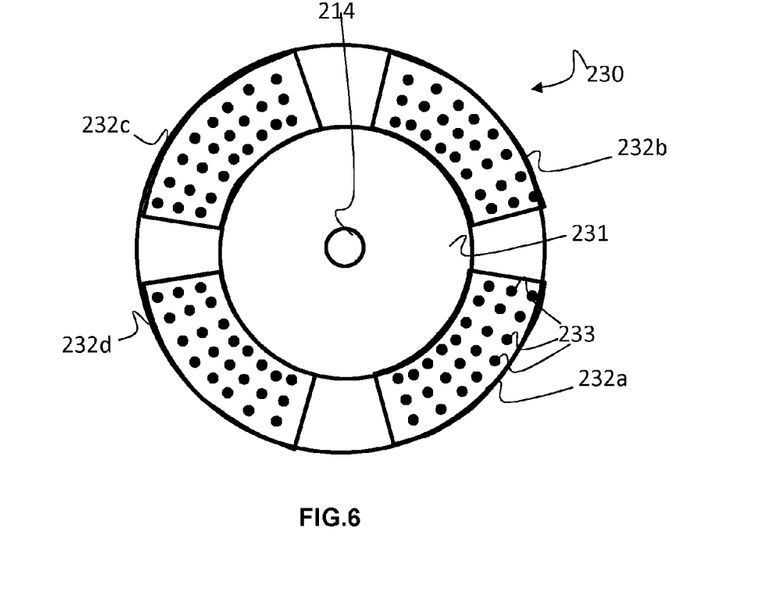
FIG. 6 represents a schematic top view of a separation baffle used to separate one stage from the other in the vessel of FIG. 3.

Some parts of the vessel can be lined with plastic material chosen amongst: polytetrafluoroethylene (PTFE) or polyfluoroalkoxy (PFA) or fluorinated ethylene propylene (FEP). For example, plate baffles 213, 233 or tubes area of the tubes bundle 212, around baffle holes 233, can be lined with such plastic material to avoid mechanical wear due to transversal shear wave, coming from the agitation system 214, between plate baffles and tubes.

The vessel that has been described allows controlling both homogeneity and temperature of the mixture and thus, obtaining a high yield for the hydrolyzing reaction in very safe conditions.

The invention claimed is:

1. A unit (130) for amidification of acetone cyanohydrin (ACH) into a mixture comprising 2-methacrylamide (MACRYDE), said unit comprising a first installation (131) for hydrolyzing acetone cyanohydrin (ACH) by sulfuric acid to produce a hydrolysis mixture comprising α-sulfatoisobutyramide (SIBAM), heating means (132) for heating said hydrolysis mixture at a temperature between 110 and 165° C., and a thermal conversion vessel (133) for thermally converting said hydrolysis mixture into said mixture comprising 2-methacrylamide (MACRYDE), wherein said first installation comprises at least one vessel (200), wherein said vessel (200) for hydrolyzing acetone cyanohydrin (ACH) by sulfuric acid ($H_2SO_4$) to produce a hydrolysis mixture comprising α-sulfatoisobutyramide (SIBAM), said vessel comprising an agitation system (214) for homogenizing the mixture, wherein said vessel comprises at least one cooling system (212) on its internal annular periphery area, said vessel divided into at least two stages, with one upper stage, along its vertical wall, each stage (S1 to S3) comprising an ACH feeding inlet (201, 202, 203) wherein said agitation system comprises a shaft equipped with two impellers (215, 216) per stage (S1 to S3) of the vessel, wherein said two impellers consist of a radial flow impeller (215) and an axial flow impeller (216).

2. The unit (130) according to claim 1, wherein said vessel comprises a bottom inlet (204) for feeding the vessel with sulfuric acid by the bottom.

3. The unit (130) according to claim 1, wherein at least one cooling system (212) comprises a vertical tubes bundle, set up in the peripheral internal annular area of the vessel, said tubes extending on the height of the vessel and being traversed by a cooling water stream.

4. The unit (130) according to claim 3, wherein said vessel comprises on its top surface, at least one water feeding duct (222) for feeding the tubes bundle of the cooling system (212) and at least one collecting duct (223) to recover water exiting tubes bundle.

5. The unit (130) according to claim 3, wherein said vessel comprises two feeding ducts (222) and two collecting ducts (223) alternatively distributed on the vessel top surface.

6. The unit (130) according to claim 1, wherein said vessel further comprises a second cooling system across an external jacket (244), said second cooling system covering the whole external surface of stages (S1 to S3), and being traversed by a cooling water stream flowing from the bottom to the top.

7. The unit (130) according to claim 1, wherein said vessel comprises a liquid overflow outlet nozzle (205) located at top of the upper stage, and a gas outlet nozzle (206) located above said liquid overflow outlet nozzle.

8. The unit (130) according to claim 1, wherein said vessel comprises a central area (221) designed to let the mixture flowing upward towards the overflow outlet nozzle (205) and to receive the agitation system (214), said the diameter of central area measuring between 40% and 80% of the vessel diameter.

9. The unit (130) according to claim 8, wherein a nozzle (241, 242, 243) is provided in each ACH feeding inlets (201, 202, 203), said nozzle allowing to inject ACH in the central area (221) of the vessel.

10. The unit (130) according to claim 9, wherein said nozzle (241, 242, 243) is located above each radial flow impeller (215).

11. The unit (130) according to claim 1, wherein said vessel comprises, between each stage (S1 to S3), a separation baffle (213, 230), which comprises a free central area (231) and holes (233) in its peripheral annular area for insertion of tubes of first cooling system (212).

12. The unit (130) according to claim 1, wherein said vessel comprises a bursting disk (225) located on top surface of the vessel (200).

13. The unit (130) according to claim 1, wherein said vessel comprises one temperature sensor (220) per stage (S1 to S3), at least one pressure sensor in gas outlet (206), one temperature sensor and one pressure sensor upward and downward each cooling system (212, 244).

14. The unit (130) according to claim 1, wherein said vessel is made of alloy selected from the group consisting of austenic alloy, austeno ferritic alloy, and tantalum alloys.

15. The unit (130) according to claim 11, wherein said baffles (213) and/or tubes area around baffle holes (233), are lined with plastic material chosen from the group consisting of: polytetrafluoroethylene (PTFE), perfluoroalkoxy (PFA) and fluorinated ethylene propylene (FEP).

16. The unit of claim 1, wherein said first installation comprises at least two vessels (200), said vessels being in parallel and functioning simultaneously.

17. The unit according to claim 1, wherein said unit comprises, downstream from the at least one vessel, a heat exchanger (305) able to cool down cooling water flowing through the cooling system(s) of the vessel, said cooling down depending on the heat generated by the exothermal reaction inside the vessel.

18. The unit according to claim 1, wherein said unit further comprises a control unit (50) which manages the regulation of the temperature of each cooling system, the regulation of temperature at each stage (S1 to S3) of the vessel (200), the measurement of the intensity of a motor (219) driving the agitation system (214), and the regulation of the feeding flowrate of sulfuric acid depending on the ACH feeding flowrates, in order to have a molar ratio of $H_2SO_4/ACH$ between 1.2 and 2.

* * * * *